United States Patent [19]

Huitema et al.

[11] Patent Number: 5,704,534
[45] Date of Patent: Jan. 6, 1998

[54] ARTICULATION ASSEMBLY FOR SURGICAL INSTRUMENTS

[75] Inventors: Thomas W. Huitema, Cincinnati; Anil K. Nalagatla, West Carrollton; Dale R. Schulze, Lebanon, all of Ohio

[73] Assignee: Ethicon Endo-Surgery, Inc., Cincinnati, Ohio

[21] Appl. No.: 724,727

[22] Filed: Sep. 30, 1996

Related U.S. Application Data

[63] Continuation-in-part of Ser. No. 359,107, Dec. 19, 1994, Pat. No. 5,632,432, and a continuation-in-part of Ser. No. 645,355, May 13, 1996.

[51] Int. Cl.⁶ .................................................. A61B 17/00
[52] U.S. Cl. .................................. 227/175.1; 227/176.1; 227/19
[58] Field of Search ........................ 227/175.1, 176.1, 227/177.1, 178.1, 179.1, 180.1, 19

[56] References Cited

U.S. PATENT DOCUMENTS

| | | | |
|---|---|---|---|
| 4,473,077 | 9/1984 | Noiles et al. | 227/19 |
| 4,728,020 | 3/1988 | Green et al. | 227/19 |
| 4,754,909 | 7/1988 | Barker et al. | 227/19 |
| 4,869,414 | 9/1989 | Green et al. | 227/19 |
| 5,271,543 | 12/1993 | Grant et al. | 227/179.1 |
| 5,312,023 | 5/1994 | Green et al. | 227/175 |
| 5,326,013 | 7/1994 | Green et al. | 227/176 |
| 5,330,502 | 7/1994 | Hassler et al. | 606/205 |
| 5,348,259 | 9/1994 | Blanco et al. | 227/19 |
| 5,374,277 | 12/1994 | Hassler | 606/207 |
| 5,381,943 | 1/1995 | Allen et al. | 227/177 |
| 5,383,888 | 1/1995 | Zvenyatsky et al. | 606/206 |
| 5,403,342 | 4/1995 | Tovey et al. | 606/205 |
| 5,405,073 | 4/1995 | Porter | 227/175.1 |
| 5,405,344 | 4/1995 | Williamson et al. | 606/1 |
| 5,409,498 | 4/1995 | Braddock et al. | 606/143 |
| 5,411,519 | 5/1995 | Tovey et al. | 606/207 |
| 5,417,203 | 5/1995 | Tovey et al. | 128/4 |
| 5,456,684 | 10/1995 | Schmidt et al. | 606/41 |
| 5,607,094 | 3/1997 | Clark et al. | 227/176.1 |

*Primary Examiner*—Joseph J. Hail, III
*Assistant Examiner*—Jay A. Stelacone
*Attorney, Agent, or Firm*—Matthew S. Goodwin

[57] ABSTRACT

An articulating surgical instrument which has an articulation transmission assembly for remotely articulating an end effector of the instrument is disclosed. Ratcheting rotation of a compressible deck within a detent housing of the assembly from a first locked position to a second locked position causes axial movement of an elongated transmission member for the articulation of the end effector from a first position to a second position angled from the first position. Also disclosed is a flexible neck assembly for articulating the end effector of the surgical instrument. Neck ribs, each having an interior plate and an exterior dish, extend from a central longitudinal rib separating a pair of flexible neck portions of the assembly. A pair of transmission band assemblies, each having an interior articulation band and an attached exterior reinforcement band, reciprocate in opposite directions within side slots of the neck ribs in response to actuation of the articulation transmission assembly. Reciprocation causes the flexible neck assembly to bend, effecting articulation. The shape of the neck ribs optimizes the radius of curvature when articulation is effected, and the reinforcement bands prevent buckling of the articulation bands.

13 Claims, 13 Drawing Sheets

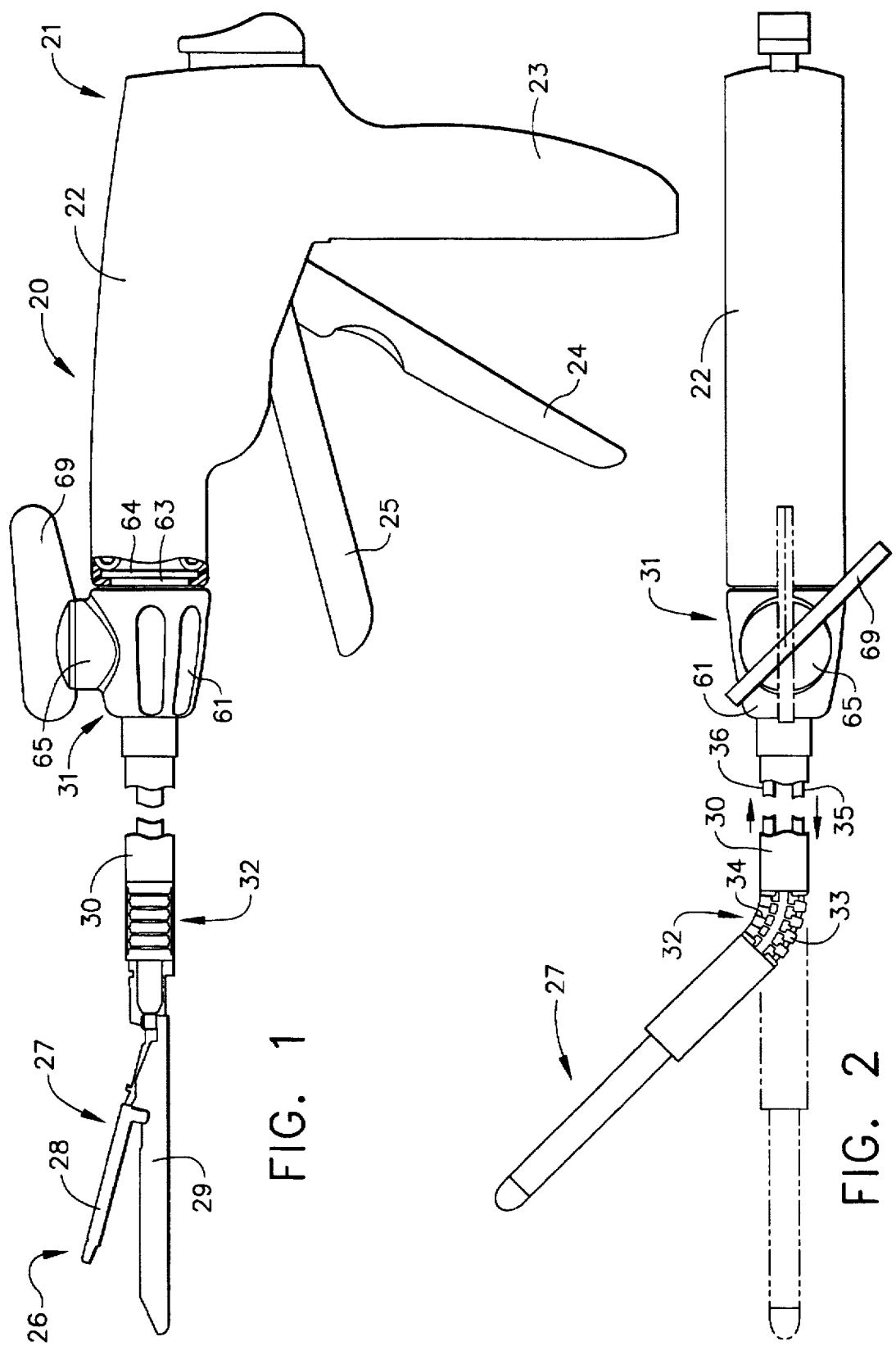

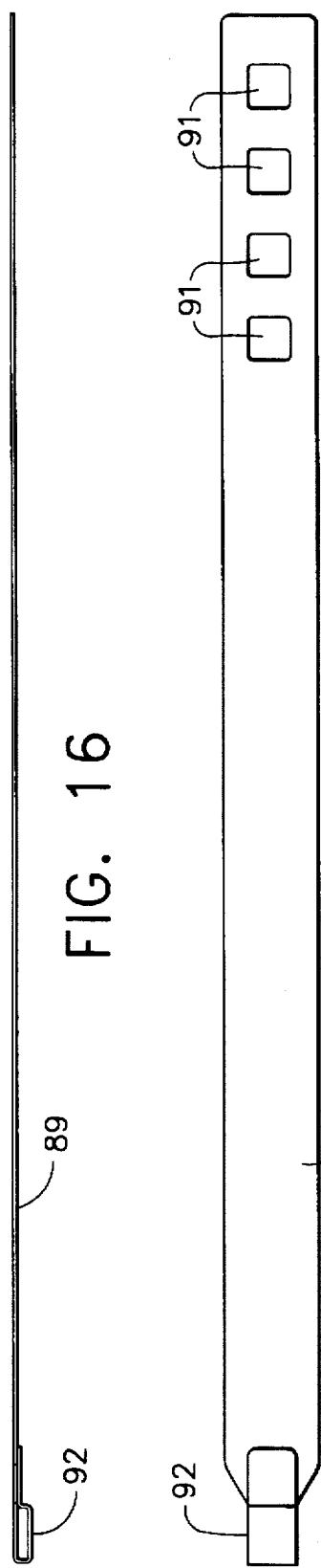
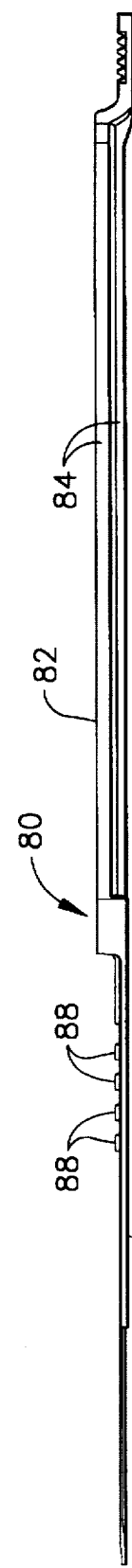
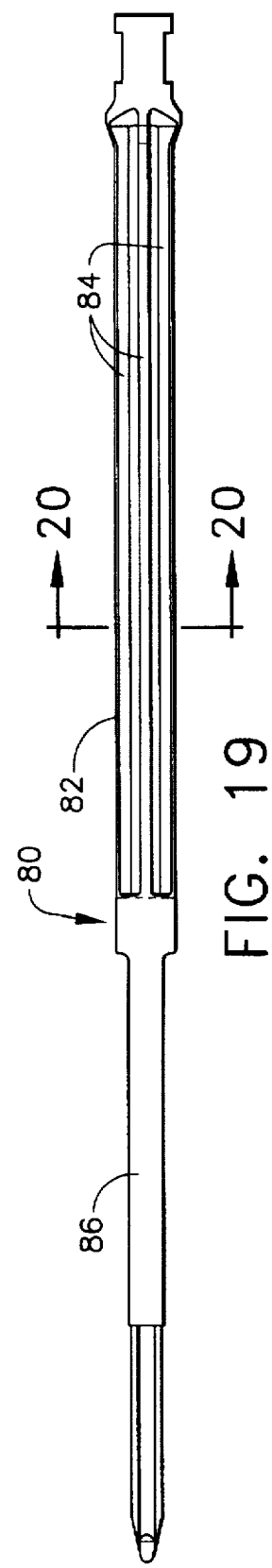

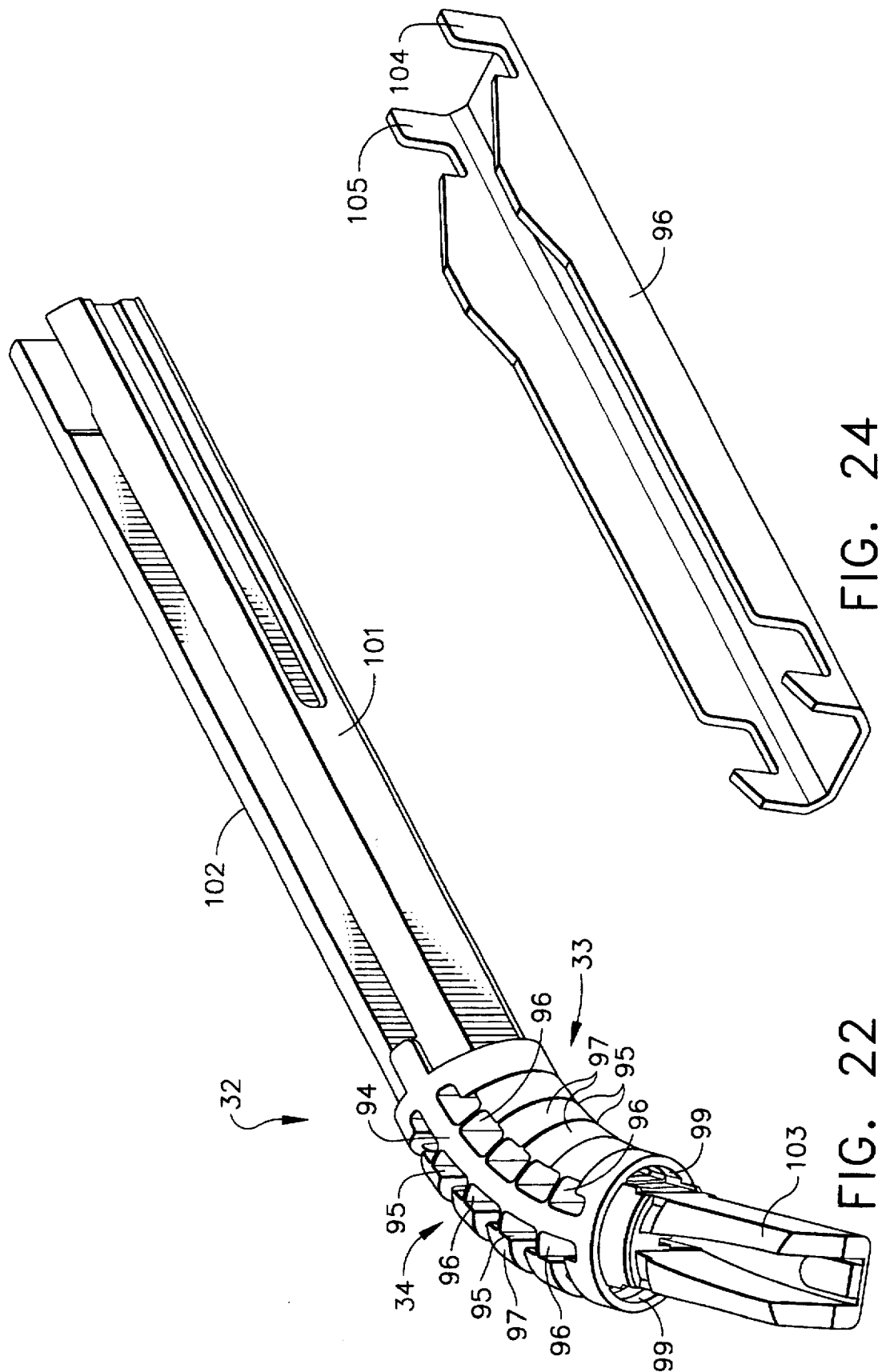

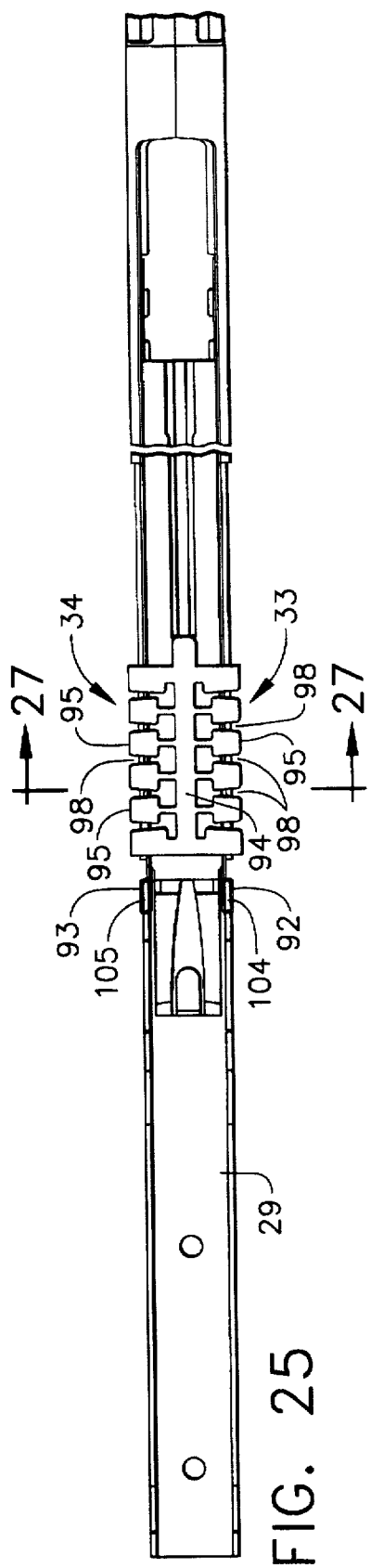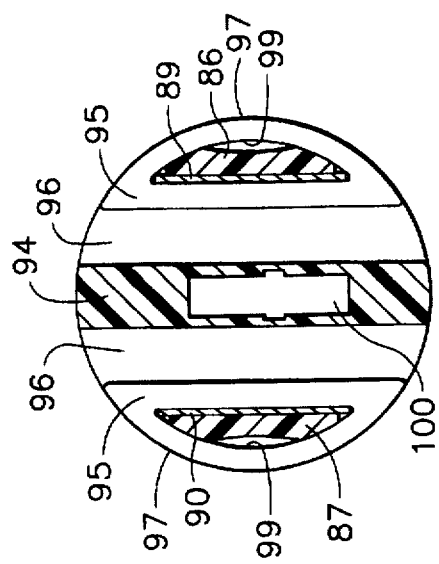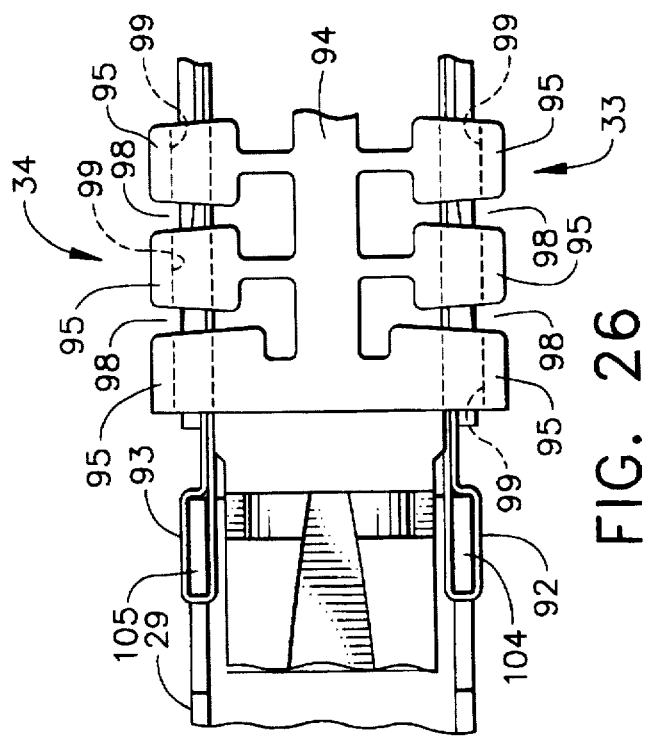

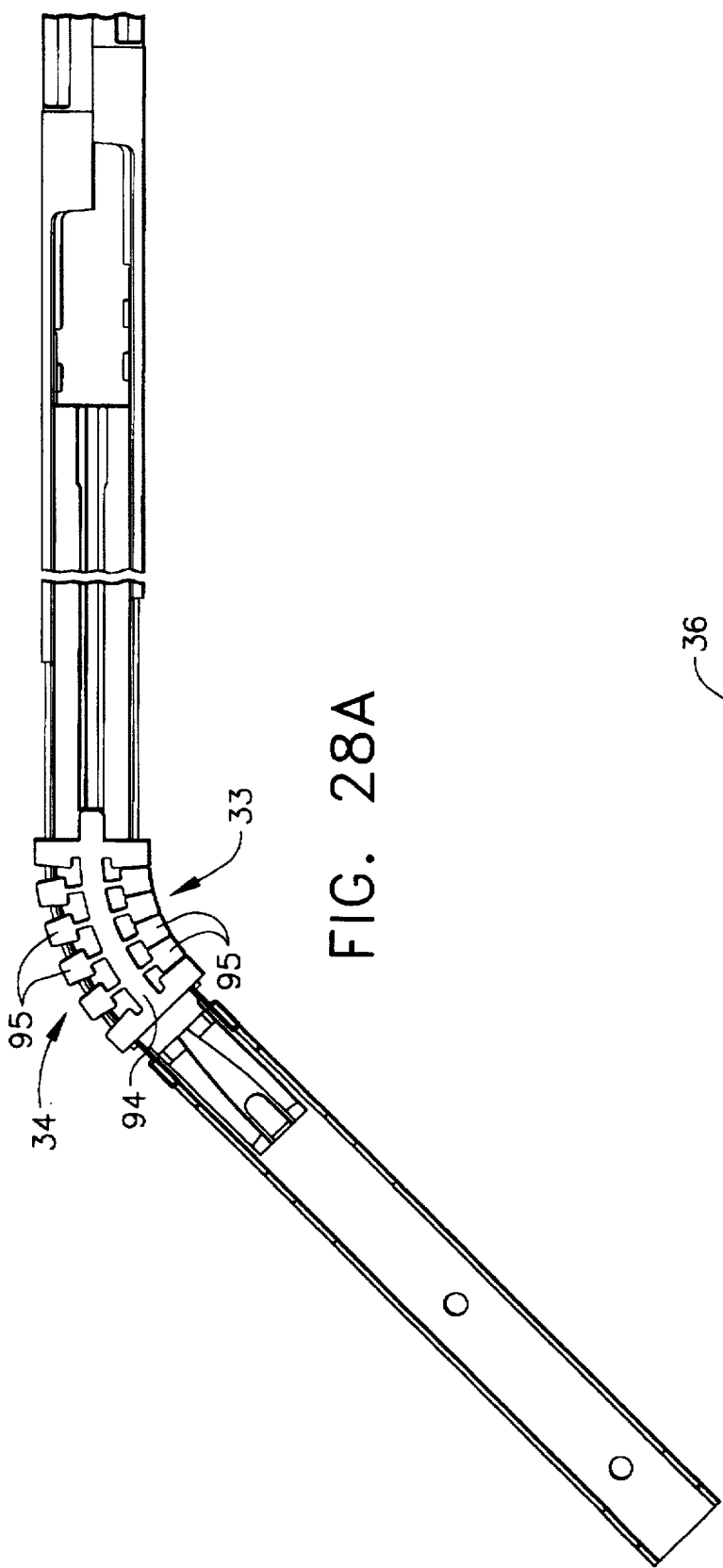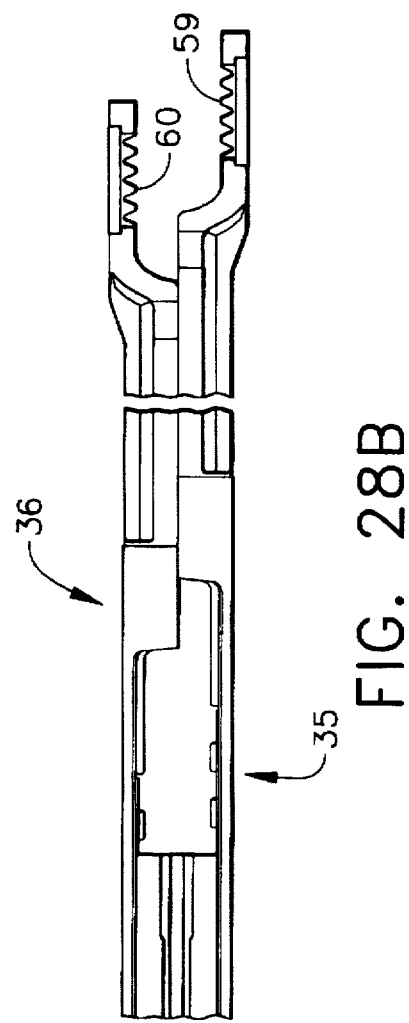
FIG. 28A
FIG. 28B 5,704,534

ARTICULATION ASSEMBLY FOR SURGICAL INSTRUMENTS

CROSS REFERENCE TO RELATION APPLICATIONS

This is a continuation-in-part of Ser. No. 08/359,107, filed Dec. 19, 1994, now U.S. Pat. No. 5,632,432; and a continuation-in-part of Ser. No. 08/645,355, filed May 13, 1996, each of which is incorporated by reference in its entirety herein.

BACKGROUND OF THE INVENTION

This invention relates to surgical instruments for performing various surgical procedures, especially endoscopic surgical procedures. In particular, it relates to the instrument mechanism which allows the surgeon to precisely position the instrument at the endoscopic surgical site conveniently and with a high degree of confidence.

During a surgical procedure, particularly an endoscopic surgical procedure, access to the surgical site within the body cavity may be provided through openings of a small diameter made in the body wall. An instrument frequently used to provide this access is the trocar. The trocar is an assembly which includes an obturator and a cannula. The obturator has a sharp tip which is used to puncture the body wall to provide the access opening. The obturator slides within the cannula, which is a hollow, cylindrical sleeve. When the obturator has punctured the body wall, the obturator is removed from the cannula. The cannula, however, remains in place within the opening made in the body wall by the obturator. Consequently, the cannula provides a cylindrical passageway to gain access to the surgical site within the body cavity.

Accordingly, a characteristic feature of many endoscopic surgical instruments is a long cylindrical shaft which can slide through the trocar cannula. At the business end of the shaft, which is the end of the instrument coming into contact with tissue at the surgical site within the body cavity, an "end effector" is provided to manipulate the tissue in some way to carry out a desired surgical procedure. The business end, including the end effector, must likewise be capable of sliding through the trocar cannula. At the opposite end of the shaft, there is an actuator operatively connected to the business end to remotely control the performance of the end effector. The actuator is conveniently housed in a frame which may include a pistol grip handle with one or more pivoting triggers. Alternatively, the actuator may include a lever, or the combination of a pivoting trigger and a lever. The actuator is activated when the surgeon pivots the trigger or depresses the lever. These actions in turn cause the end effector to perform its desired function.

Before the surgeon can actuate the end effector to manipulate tissue to perform a desired surgical procedure, the end effector must be carefully positioned at the desired location within the endoscopic surgical site. It also must be positioned at a proper orientation if, for example, staples must be fired in a certain direction to properly fasten the tissue. Therefore, endoscopic surgical instruments typically include mechanisms to enable the surgeon to vary the orientation and positioning of the end effector at the business end of the instrument. Of course, the mechanisms must be operable at or near the frame of the instrument so that the surgeon can easily manipulate and control these mechanisms while gripping the instrument with his hand.

Often, it may be desirable to rotate the end effector of an endoscopic surgical instrument about the long axis of the shaft of the instrument to vary the orientation of the end effector. Accordingly, many endoscopic surgical instruments include a knob or dial on or adjacent the frame which, when actuated by the surgeon's hand, rotates the shaft of the instrument and correspondingly rotates the end effector.

Another critical feature of certain endoscopic instruments is the ability to pivot the end effector so that the end effector is positioned at an "articulated" position relative to the long axis of the shaft. Consequently, endoscopic instruments often include an articulation knob or dial on or near the frame for remotely articulating the end effector for precise positioning of the end effector within the endoscopic surgical site. Numerous examples of these articulation mechanisms for endoscopic surgical instruments abound. For example, the reader is encouraged to review U.S. Pat. Nos. 4,728,020; 4,869,414; 5,312,023; 5,326,013; 5,330,502; 5,374,277; 5,381,943; 5,383,888; 5,403,342; 5,405,344; 5,409,498; 5,411,519, 5,417,203 and 5,456,684. Articulating mechanisms for pivoting the end effector are also described in co-pending U.S. Ser. No. 08/259,322, filed Jun. 10, 1994, now U.S. Pat. No. 5,601,224; and Ser. No. 08/442,783, filed May 18, 1995, now U.S. Pat. No. 5,626,587.

Although articulating endoscopic surgical instruments are now freely available in commerce and have been described in the literature, it would be advantageous if an articulation assembly could be optimized to deliver reliable and efficient articulation. Also, the mechanisms which control articulation typically have a significant drawback, and it would be beneficial to overcome this particular drawback. Specifically, when the end effector of the instrument is articulated to a desired position, the end effector is often pushed against the tissue before the end effector is manipulated to perform the desired surgical function. In some cases, the surgeon intentionally uses the articulated end effector to push against the tissue because the surgeon desires to retract or dissect tissue to provide sufficient space within the site for accurately manipulating the end effector to perform the surgical function. Unfortunately, what often occurs when a force is applied to the end effector in an articulated position is that the end effector is forced from its desired articulated position. In other words, the end effector "unwinds" from its desired articulated position, and may shift to another undesired articulated position or revert back to its original, unarticulated position. Obviously, this is a nuisance which would be desirable to overcome.

In addition, when resistance to movement from an articulated position is provided in the articulation assembly to maintain proper positioning (as described in U.S. Pat. No. 5,601,224 discussed above), a corresponding resistance must likewise be provided when the surgeon articulates the end effector to its desired articulated position. In other words, the surgeon must apply a greater force or torque on the articulation knob or dial in order to provide a corresponding increase in the resistance of the end effector to movement from the articulated position.

Furthermore, if too great a force is applied to the end effector in an articulated position, not only may the end effector unwind, but also the components of the articulation assembly may break, leading to a catastrophic failure.

Accordingly, a surgical instrument is needed which characteristically includes an end effector at the business end of the shaft which is capable of being remotely articulated to properly position the end effector. In particular, the optimization of the articulation assembly of the instrument to precisely position the end effector is needed. The ability to remotely articulate the end effector is especially important for endoscopic surgical instruments, which characteristically include an elongated cylindrical shaft separating the frame of the instrument from the end effector. Significantly, the mechanism for articulation would desirably resist movement of the end effector in an articulated position when a force is applied to the end effector. Additionally, resistance would be provided without requiring excessive force to position the end effector from an unarticulated to an articulated position. Furthermore, it would be desirable if a fail safe mechanism to prevent component breakage were provided which could reset the articulation assembly if too great a force were applied to the articulated end effector.

SUMMARY OF THE INVENTION

In its broadest sense, the invention is an articulating surgical instrument which comprises an articulation transmission assembly. The articulation transmission assembly remotely articulates an end effector of the instrument. The articulation transmission assembly has a detent housing, a compressible deck, an actuator and a drive member. Each of these components of the articulation transmission assembly will now be described briefly.

The detent housing is mounted on the instrument. It contains a plurality of detent teeth in the housing.

The compressible deck contains a plurality of ratchet teeth on the deck. The deck teeth are matingly coupled with the detent teeth of the detent housing when the articulation transmission assembly is in a first lock position.

The actuator is fitted on the detent housing. It applies a rotational force on the deck. When such a rotational force is applied to the deck by the actuator, the deck compresses. As the deck compresses, the deck teeth decouple from the detent teeth. The decoupling of the teeth facilitate ratcheting rotation of the deck from the first locked position to a second locked position.

Finally, the drive member of the articulation transmission assembly is in communication with the deck. It translates rotational movement of the deck into axial movement of an elongated transmission member which is attached to the drive member.

The articulation transmission assembly of the surgical instrument of this invention provides the surgeon with the ability to remotely articulate the end effector of the instrument. Rotation of the actuator provides axial movement of the elongated transition member to articulate the end effector.

Significantly, rotation of the actuator of the articulation transmission assembly decouples the teeth of the deck from the detent housing to significantly reduce the resistance to rotation. Consequently, when rotational resistance is reduced, the desired articulation of the end effector is more readily facilitated. If a rotational force is not applied to the actuator, the articulation transmission assembly rests in a locked position. When the end effector is in a locked, articulated position, a greater force must be applied on the end effector to decouple the teeth and consequently change the articulated position because the deck will not be subjected to compression resulting from rotation of the actuator. Therefore, when the surgeon wants to rotate the actuator for articulation, the resistance to rotation is significantly less than the resistance which must be overcome when a force is applied to the articulated end effector.

In addition, the articulation transmission assembly of the surgical instrument provides for ratcheting rotation of the end effector. Since force can be applied to decouple the teeth of the deck from the teeth in the detent housing, the amount of total force which the components of the articulation transmission assembly is subjected can be limited. Consequently, the articulation transmission assembly of this invention provides a fail-safe mechanism to prevent component breakage.

In a preferred embodiment of this invention, an articulating surgical instrument particularly adapted for endoscopic surgery is provided. The instrument comprises a frame which includes a hand grip for gripping and manipulating the instrument at a first end of the instrument. An elongated endoscopic shaft extends from the frame. The shaft has a longitudinal axis. The instrument has an end effector in communication with the shaft at an opposite end of the instrument for manipulating tissue to carry out a desired surgical function. The end effector is movable to provide articulation of the end effector from a first position parallel to the shaft longitudinal axis to a second position angled from this axis.

The preferred instrument has an articulation transmission assembly adjacent the frame for remotely articulating the end effector from the first position to the second position. This articulation transmission assembly includes a nozzle and an articulation body. The nozzle is coupled to the shaft and secured to the frame. It has a body with a bore extending through it generally parallel to the shaft longitudinal axis. It also has a detent housing extending from the nozzle body. The detent housing contains a plurality of detent teeth in the housing. The articulation body is mounted within the detent housing of the nozzle body for rotational movement from a plurality of locked positions spaced between a plurality of unlocked positions. The articulation body includes a deck, a drive member and a lever. A brief description of these components will now be set forth.

The deck has a pair of spaced-apart deck halves separated by mutually-opposed first and second detents. Each of the deck halves has a plurality of deck teeth. The deck teeth are positioned for interacting relationship with the detent teeth of the detent housing. When the articulation body is in one of the locked positions, the deck teeth mesh with the detent teeth. In contrast, when the articulation body is in one of the unlocked positions, the deck teeth do not mesh with the detent teeth.

The drive member of the articulation body is coupled to the deck. The drive member descends into the bore of the nozzle body. It has first and second elongated transmission members attached to it. These transmission members extend through the bore into the shaft for remotely articulating the end effector in response to actuation of the articulation transmission assembly.

Finally, the lever of the articulation transmission assembly is secured to the articulation body for rotating the articulation body within the detent housing of the nozzle. The lever includes a cap fitted on the detent housing. The cap contains a slot within the cap for receiving the first and second detents of the deck halves so that the deck halves of the deck are attached to the cap.

Significantly, when a rotating force is applied to the lever of the articulation transmission assembly, the slot in the cap urges the first and second detents toward each other. In so doing, the deck teeth are withdrawn from the detent teeth, and rotation of the articulation body within the detent housing from the locked positions to the unlocked positions is therefore facilitated.

The preferred embodiment of the instrument of this invention is particularly adapted for endoscopic surgery because it facilitates the remote articulation of the end effector adjacent the frame of the instrument. In addition, the use of the slot in the cap of the lever to urge together the deck halves to withdraw the teeth of the deck from the teeth in the detent housing is a simple and effective mechanism for reducing the rotational forces which the surgeon must apply to the lever when he wants to articulate the end effector. In effect, the spaced-apart deck halves of the articulation body provide a compressible deck assembly within the articulation body. When the lever is rotated, the walls of the slot apply a compressive force on the first and second detents of the deck halves to urge the deck halves together. Thus, the deck teeth are readily withdrawn from the detent teeth.

In another preferred embodiment of this invention, the invention is an articulating surgical instrument comprising a frame including a hand grip for gripping and manipulating the instrument at a first end of the instrument, a shaft extending from the frame, and an end effector at an opposite end of the instrument for manipulating tissue to carry out a desired surgical function. The end effector is movable to provide articulation of the end effector from a first position generally parallel to the longitudinal axis of the shaft to a second position angled from the shaft longitudinal axis. Significantly, the articulating surgical instrument also comprises a flexible neck assembly coupled to a proximal end of the end effector for articulating the end effector from the first position to the second position.

The flexible neck assembly includes first and second flexible neck portions, and first and second transmission band assemblies. The first and second flexible neck portions of the assembly are separated by a central longitudinal rib between these neck portions. Each of the flexible neck portions has a plurality of neck ribs extending from the central longitudinal rib, and a plurality of kerfs separating each of the neck ribs from an adjacent neck rib. Each of the neck ribs has a side slot through it. The first and second transmission band assemblies are received within each slide slot of the neck ribs of the first and second flexible neck portions for reciprocating movement within the slots. Each of the transmission band assemblies has an interior articulation band and an exterior reciprocation band attached to the interior band.

When the first and second transmission band assemblies are reciprocated in opposite directions within each side slot of the neck ribs of the first and second flexible neck portions of the flexible neck assembly, the end effector is consequently articulated from the first position to the second position.

The flexible neck assembly of the articulating surgical instrument of this invention optimizes the delivery of reliable and efficient articulation to precisely position the end effector of the instrument as needed or desired during a surgical procedure. When the first and second transmission band assemblies are reciprocated in opposite directions within the side slots of the neck ribs, the flexible neck assembly is caused to bend. As it bends, it effects the articulation of the end effector. Advantageously, the attachment of the exterior reinforcement bands to the interior articulation bands optimizes performance of the flexible neck assembly because the reinforcement bands minimize or prevent the articulation bands from buckling when the flexible neck assembly is bent in response to the reciprocating movement in opposite directions of the first and second transmission band assemblies.

In yet another preferred embodiment of this invention, the neck ribs of the first and second flexible neck portions of the flexible neck assembly of the articulating surgical instrument are configured as semi-circular disks extending from the central longitudinal rib. Each of these semi-circular disks of the neck ribs has an interior plate extending generally perpendicularly from the central longitudinal rib and parallel to an adjacent interior plate, and a concave exterior dish extending from the interior plate.

The particular configuration of the neck ribs which has been described in the preceding paragraph optimizes the bending movement of the flexible neck assembly, and therefore improves the overall performance of the articulating surgical instrument. Specifically, the plates of the neck ribs allow greater spacing between adjacent plates, and therefore the radius of curvature of the flexible neck assembly can be increased when the assembly is caused to bend during articulation. Correspondingly, the exterior dishes of the neck ribs enable smooth articulation over a fixed angle from the longitudinal axis of the shaft of the instrument.

In the most preferred embodiment of this invention, the end effector of the surgical instrument of this invention is a surgical fastening assembly, and the instrument is an articulating surgical stapler particularly adapted for endoscopic surgery. The surgical fastening assembly has an elongated anvil facing an elongated channel for receiving a staple cartridge. The surgical fastening assembly is capable of clamping tissue, and then firing staples into the clamped tissue.

The instrument of this invention can be used in any surgical application where it is desirable to articulate an end effector of the instrument to better position the end effector at the surgical site. Remote articulation is particularly desired for endoscopic surgical applications, although it may also be desirable for conventional, open surgical procedures.

BRIEF DESCRIPTION OF THE DRAWINGS

FIG. 1 is a foreshortened side elevational view of the preferred articulating surgical stapler of this invention. A portion of the frame of the stapler has been exposed to show the attachment of the articulation transmission assembly of the stapler to the frame.

FIG. 2 is a plan view of the stapler of FIG. 1 illustrating the remote articulation of the surgical fastening assembly of the stapler in response to the actuation of the articulation transmission assembly.

FIG. 16 is a plan view of the first interior articulation band illustrated in FIG. 15.

FIG. 17 is an exterior side elevation view of the interior articulation band of FIG. 16.

FIG. 18 is a plan view of the first transmission band of the first transmission band assembly illustrated in FIG. 15.

FIG. 19 is an exterior side elevation view of the first transmission band of FIG. 18.

FIG. 22 is a perspective view of the flexible neck assembly, excluding the attachment of the transmission band assemblies, shown in an articulated position.

FIG. 24 is an isometric view of the channel for seating the staple cartridge of the stapler.

FIG. 25 is a plan view of the distal end of the stapler including a portion of the preferred flexible neck assembly. A mid portion of the assembly has been broken away to shorten and enlarge the illustration.

FIG. 26 is an enlarged fragmentary plan view of the coupling of the distal end of the interior articulation bands and the cartridge channel.

FIG. 27 is a section view taken along line 27—27 of FIG. 25.

FIGS. 28A and 28B are plan views of the flexible neck assembly, coupled to the cartridge channel, shown in an articulated position. Each view has been foreshortened for enlarged illustration.

DETAILED DESCRIPTION OF THE PREFERRED EMBODIMENT

Figure 3:
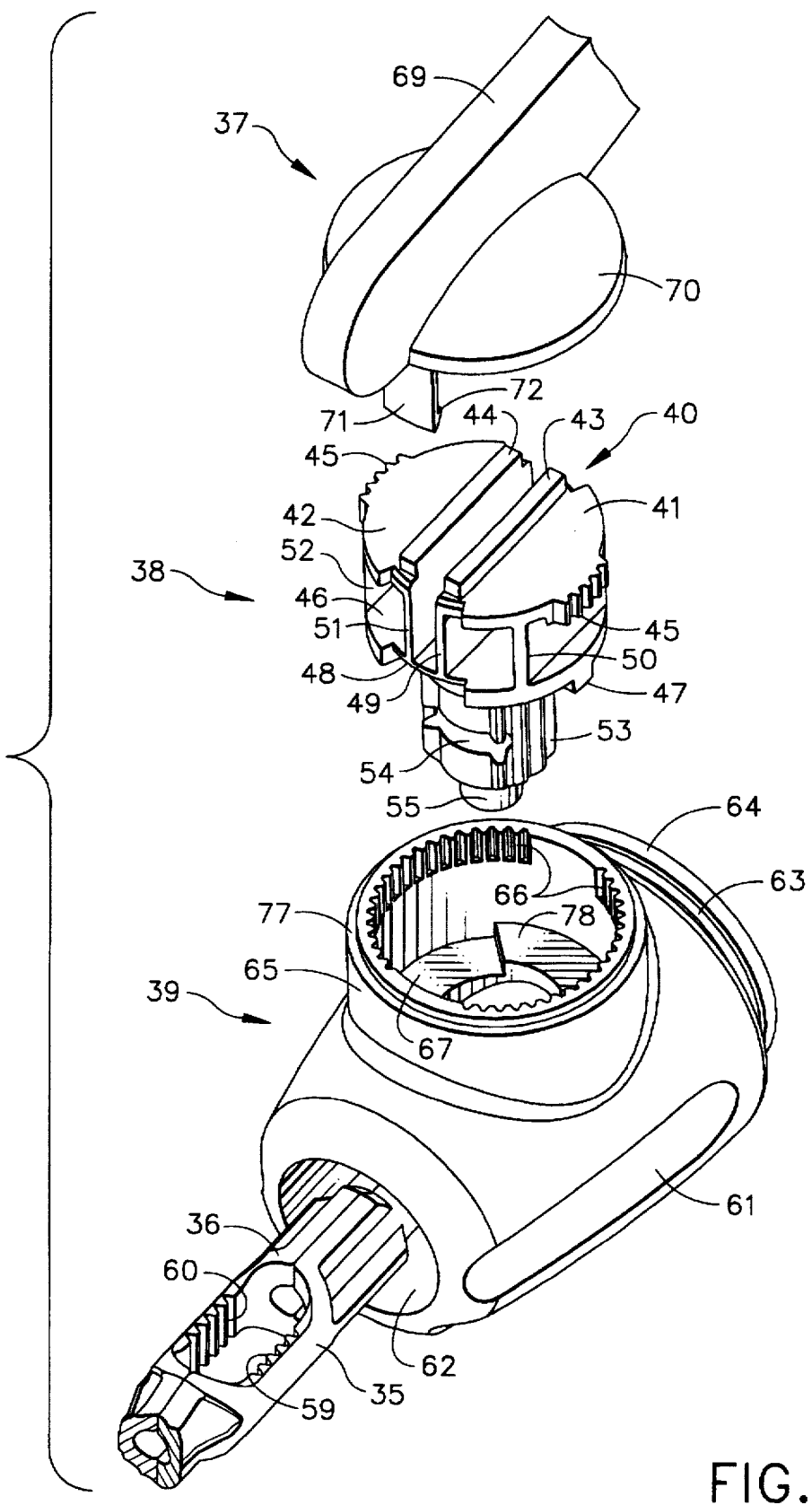
FIG. 3 is an exploded isometric view of the articulation transmission assembly of the stapler of FIG. 1.

Referring initially to FIG. 1, there is shown the preferred articulating endoscopic stapler 20 of this invention. At a first proximal end 21, the stapler has a frame 22 adapted to enable the user to grip and manipulate the stapler. The frame has a stationary hand grip 23 for placement in the palm of the user's hand, and pivotally mounted clamping and firing triggers, 24 and 25, for remotely clamping tissue and firing staples into the clamped tissue, respectively.

At an opposite distal 26 end of the stapler 20 there is the end effector in the form of a surgical fastening assembly 27. The surgical fastening assembly has an elongated anvil 28 facing an elongated channel 29 adapted to receive a surgical cartridge containing a plurality of staples therein (surgical cartridge not shown). Extending from the frame 22 of the stapler and coupling the frame to the surgical fastening assembly 27 is an elongated endoscopic shaft 30.

The preferred actuation assembly within the frame of the stapler for remotely clamping tissue and firing staples into the clamped tissue in response to pivotal counterclockwise rotation of the clamping and firing triggers is described in U.S. Pat. No. 5,465,895 and commonly assigned, co-pending application Ser. No. 08/431,105, filed Apr. 28, 1995, both of which are incorporated into this specification by reference. The preferred clamping mechanism within the surgical fastening assembly to urge the anvil from a first position spaced from the elongated channel to a second position adjacent the channel is described in commonly assigned, co-pending application Ser. No. 08/530,931, filed Sep. 19, 1995, which is also incorporated into this specification by reference.

Referring to FIGS. 1 and 2, the preferred articulating stapler 20 has an articulation transmission assembly 31 coupling the frame 22 to the elongated endoscopic shaft 30 of the stapler. When the articulation transmission assembly is rotated, it causes the remote articulation of the surgical fastening assembly 27 of the stapler. The elongated endoscopic shaft contains a flexible neck assembly 32 enabling the articulation of the surgical fastening assembly 27 of the stapler. The flexible neck assembly has first and second flexible neck portions, 33 and 34, which receive first and second elongated flexible transmission band assemblies, 35 and 36. Upon rotation of the articulation transmission assembly, one of the first and second flexible transmission band assemblies is moved forwardly and the other band assembly is moved rearwardly. In response to the reciprocating movement of the band assemblies within the first and second flexible neck portions of the flexible neck assembly, the flexible neck assembly bends to provide articulation. A further description of the flexible neck in an articulating endoscopic stapler is described in parent patent application Ser. No. 08/539,107, filed Dec. 19, 1994, and in the detailed description provided below.

The component parts of the articulation transmission assembly 31 are illustrated in FIG. 3. The major components of the assembly are an actuator 37, an articulation body 38 and a nozzle 39. Rotational movement of the actuator 37 causes corresponding rotation of the articulation body 38 within the nozzle 39. The first and second elongated transmission band assemblies, 35 and 36, consequently reciprocate axially in opposite directions parallel to the longitudinal axis of the endoscopic shaft 30 of the stapler to cause the remote articulation of the surgical fastening assembly through the flexible neck assembly of the endoscopic shaft.

Figure 6:
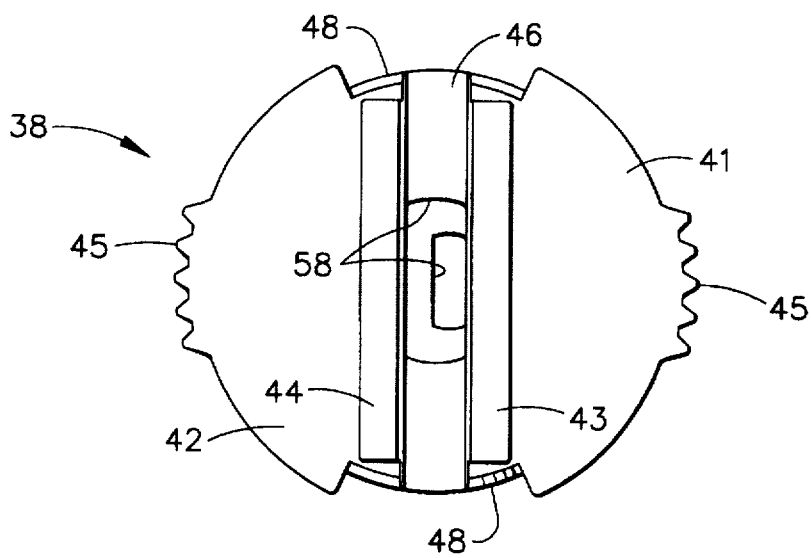
FIG. 6 is a plan view of the articulation body of the articulation transmission assembly of FIG. 3.
Figure 7:
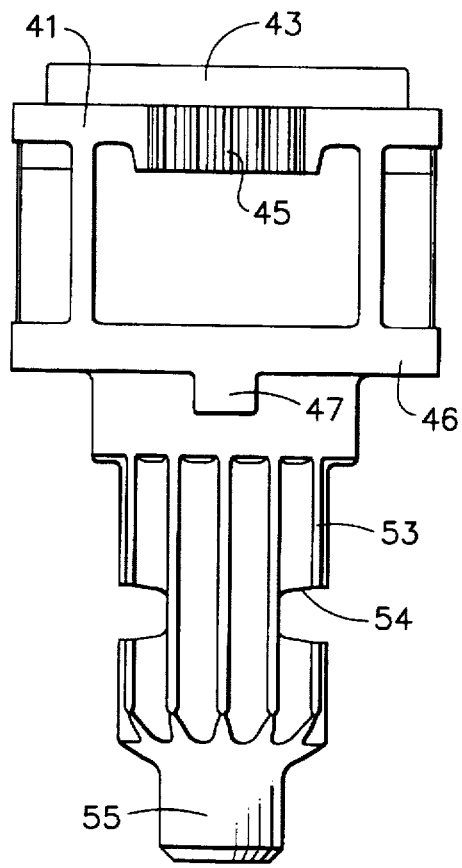
FIG. 7 is a side elevational view of the articulation body of FIG. 6.
Figure 8:
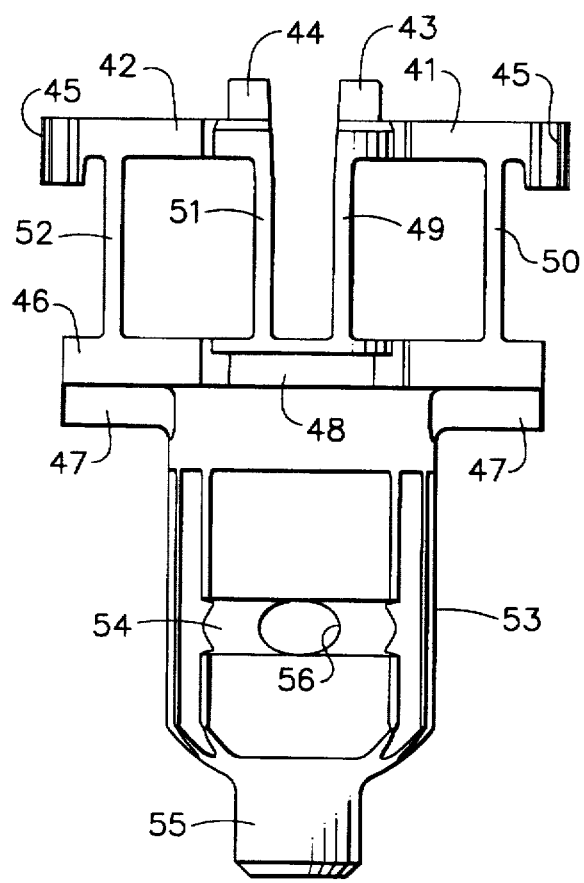
FIG. 8 is a front elevational view of the articulation body of FIG. 6.

Referring specifically to FIG. 3 in combination with FIGS. 6–8, a detailed illustration of the articulation body 38 is provided. The articulation body has a deck 40 consisting of first and second spaced-apart, semicircular deck halves, 41 and 42. The deck halves are mutually opposed to each other and essentially represent mirror images of each other. The first and second deck halves have protruding from their surfaces mutually opposed first and second detents, 43 and 44. Each deck half has a set of deck teeth 45 spaced about 180° from the set of deck teeth on the other deck half.

The articulation body also has a generally circular base 46. The base has a pair of rotation stops 47 descending from its surface as well as a pair of finger recesses 48. The base 46 flexibly supports the deck 40 on two sets of beams. First inner and outer flexible beams, 49 and 50, extend upwardly from the base and are integrally attached to the first deck half 41. Likewise, second inner and outer flexible beams, 51 and 52, extend upwardly from the base and are integrally attached to the second deck half 42. The first and second outer flexible beams, and the first and second inner flexible beams, are displayed in mutually opposed relationship.

Again focusing on FIG. 3 and FIGS. 6≧8, the articulation body 38 further includes a drive gear 53 descending from the base 46. The drive gear has a flared opening 54 through it, and a lower pivot 55. Within the flared opening of the drive gear, there is a firing rod orifice 56 for receiving the firing rod 57 enabling the firing of staples into the clamped tissue in response to pivotal rotation of the firing trigger (see FIG. 12). Coring cavities 58 are embedded in the base for manufacturing optimization. The drive gear is coupled to first and second drive racks, 59 and 60, on the flexible elongated transmission band assemblies, 35 and 36, to effect the desired reciprocating movement of the bands.

Figure 9:
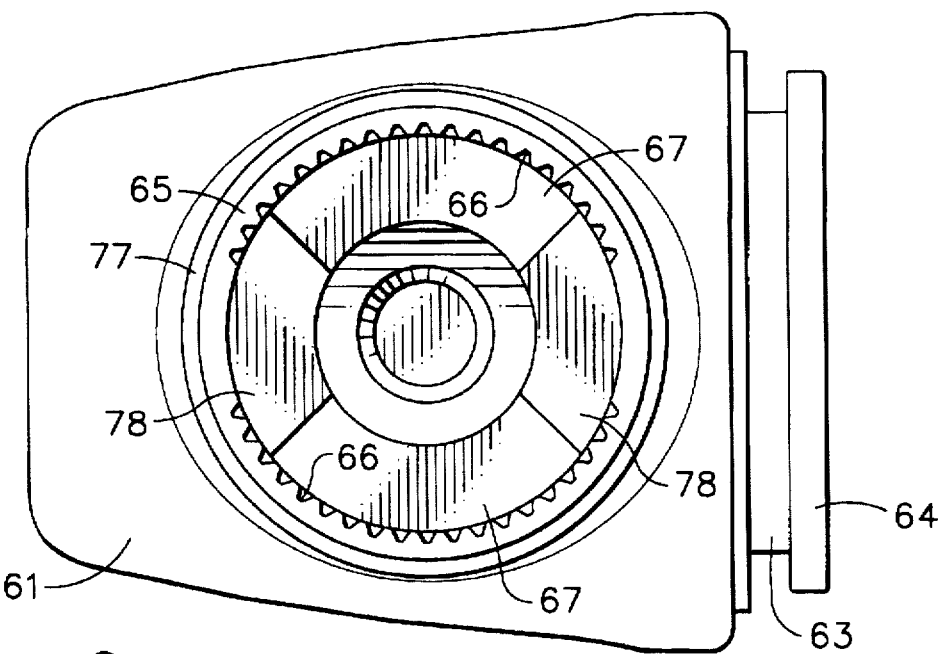
FIG. 9 is a plan view of the nozzle of the articulation transmission assembly of FIG. 3.
Figure 10:
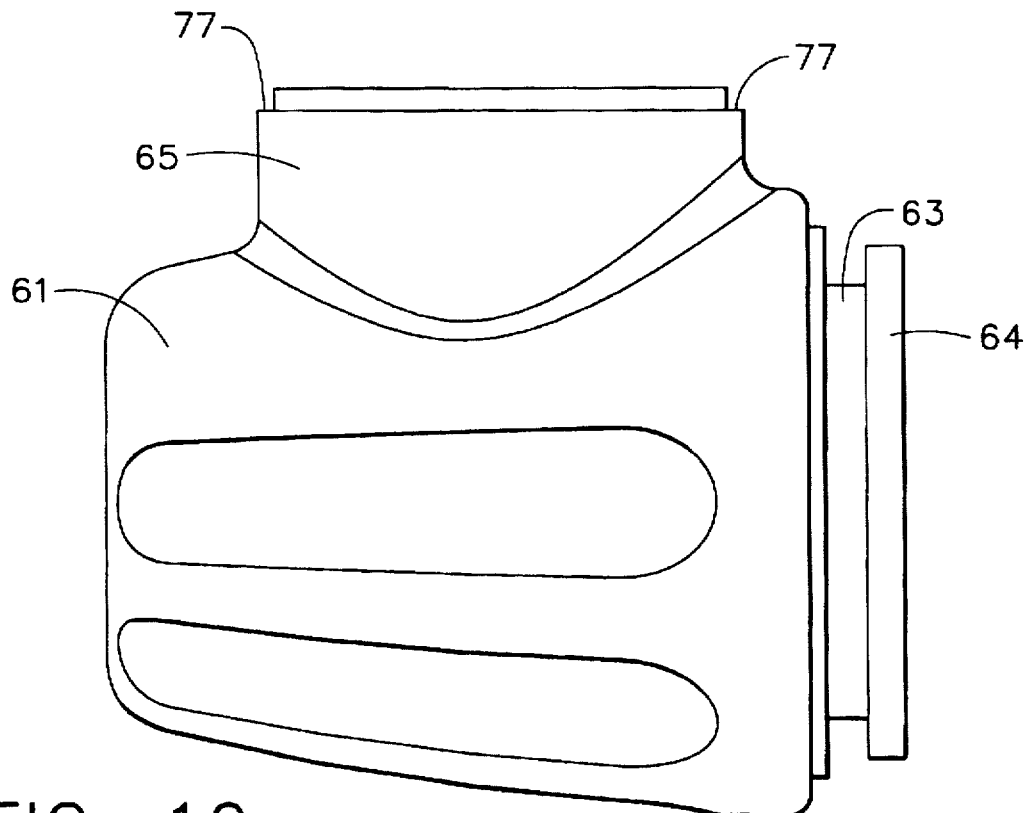
FIG. 10 is a side elevational view of the nozzle of FIG. 9.

The nozzle 39 of the articulation transmission assembly is specifically illustrated in FIG. 3 in combination with FIGS. 9 and 10. The nozzle has a nozzle body 61. The nozzle body has an axial bore 62 extending through it for receiving the drive gear 53 of the articulation body 38. The bore provides a continuous opening axially from the frame into the elongated endoscopic shaft, and therefore the firing rod 57 and other operative components of the stapler can communicate with the surgical fastening assembly 27 from the frame 22. The nozzle body also has a frame groove 63 and flange 64 to fasten the body of the articulation transmission assembly to the frame (see FIG. 1).

Extending from the nozzle body 61 of the nozzle 39 is a detent housing 65. Within the housing, there is an annular array of detent teeth 66. Spaced from the detent teeth is a detent housing floor 67. The floor 67 is displayed adjacent to the nozzle body 61. It has a pair of ledges 78 which interact within the rotation stops 47 of the articulation body to limit the degree of rotation. When the articulation body is inserted into the detent housing, the base of the articulation body sits on the floor within the detent housing, and the deck teeth 45 of the first and second deck halves, 41 and 42, of the deck 40 are aligned with the detent teeth 66 of the detent housing to provide an essentially continuous surface. Additionally, when the articulation body is inserted, the lower pivot 55 of the drive gear 53 is received in a pivot hole 68 located interiorly within the nozzle body adjacent to the axial bore 62 (see FIG. 12).

Figure 4:
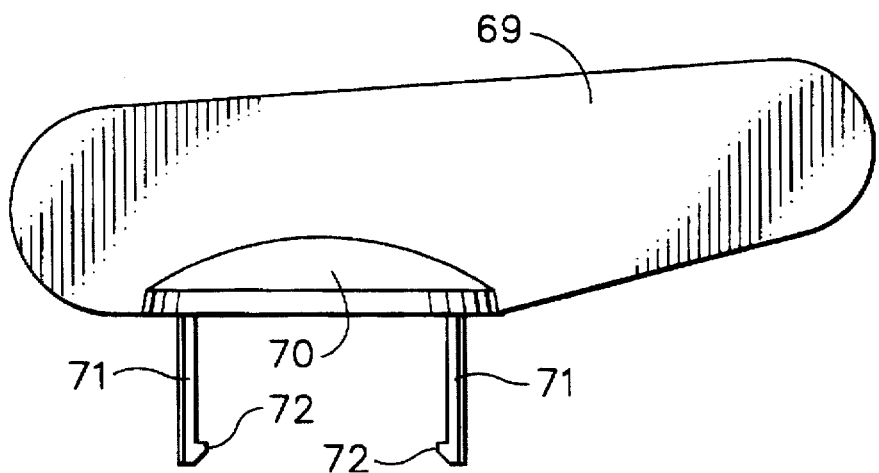
FIG. 4 is a side elevation view of the lever cap of the articulating transmission assembly of FIG. 3.
Figure 5:
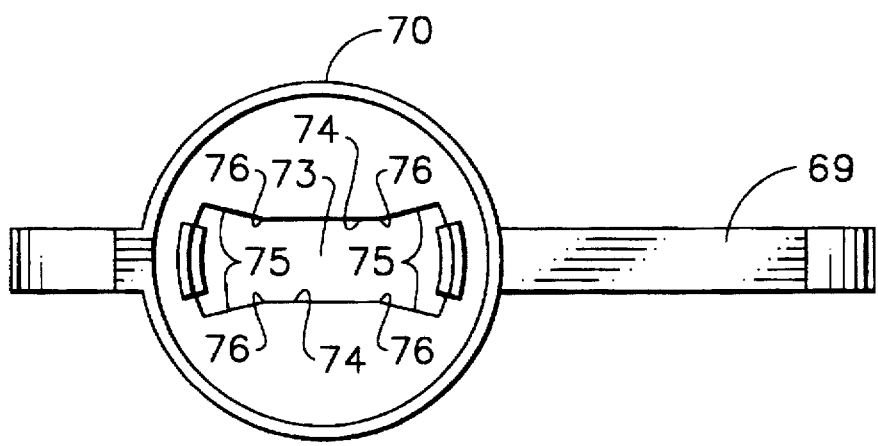
FIG. 5 is a bottom view of the lever cap of FIG. 4.

FIG. 3 in combination with FIGS. 4 and 5 illustrate the actuator 37 of the articulation transmission assembly. The actuator consists of a lever arm 69, a circular cap 70 and a pair of retaining fingers 71. The lever arm is mounted on the top of the cap. The pair of retaining fingers descend downwardly from the underside of the cap. Each of the retaining fingers has a retaining clip 72. The retaining fingers are received within the finger recesses 48 of the articulation body 38. The underside of the cap (FIG. 5) has a slot depression 73 embedded within the cap. The slot depression is bounded by a pair of parallel slot walls 74 and diagonal flats 75. Pressure points 76 are consequently provided at the junction between the parallel walls and the diagonal flats.

The first and second detents, 43 and 44, of the deck halves of the articulation body are inserted into the slot depression 73 within the underside of the circular cap 70. Accordingly, the parallel slot walls 74 frictionally contact the first and second detents of the deck, thus securing the actuator 37 to the articulation body 38. Further, when the articulation body is inserted into the detent housing 65 of the nozzle body 61 so that the articulation body is retained when the firing rod 57 is received through the firing rod orifice 56 of the drive gear 53, the cap 70 is secured onto the detent housing when the cap rests on an actuator cap lid 77 of the detent housing.

Advantageously, each of the three significant components of the articulation transmission assembly, namely the actuator, articulation body and nozzle, are injection molded components. The preferred material of construction for each of the components is a glass fiber-reinforced amorphous polyamide, sold commercially under the trade name Grivory GV-4H by EMS—American Grilon as of the date upon which the application which matured into this patent was filed.

Figure 11:
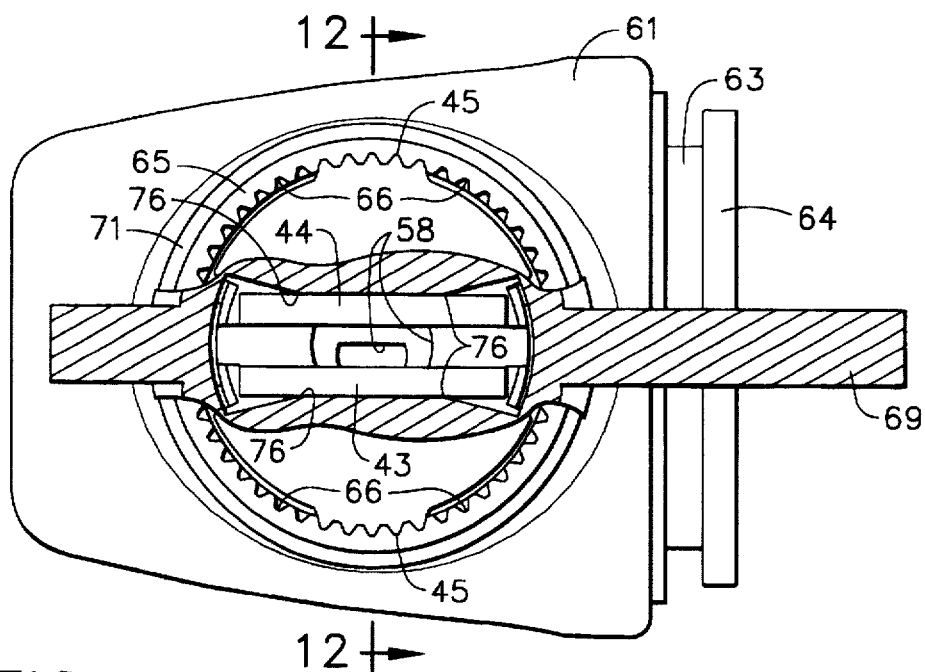
FIG. 11 is a plan view of the articulation transmission assembly of the stapler of FIG. 1 in which the articulation body of the assembly is shown in a locked position. The lateral sides of the lever cap have been truncated to illustrate the internal details of the assembly. The top of the lever cap has been further sectioned away to illustrate the interface between the cap and the articulation body.
Figure 12:
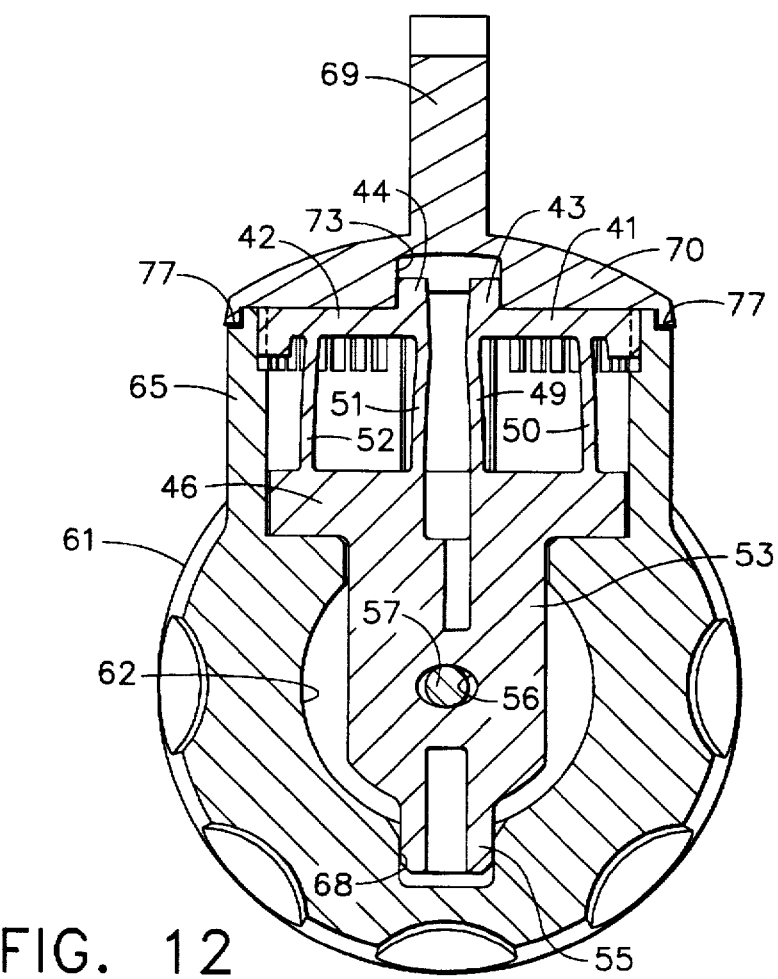
FIG. 12 is a transverse section of the articulation transmission assembly generally taken along line 12—12 of FIG. 11. The articulation body of the assembly is shown in the locked position to prevent the surgical fastening assembly of the stapler from changing articulation angle.

Referring now to FIGS. 11 and 12, there is shown the articulation transmission assembly 31 of the stapler 20 when the assembly is in a locked position. In this locked position, the deck teeth 45 of the articulation body 38 are matingly coupled to, and mesh with, the detent teeth 66 of the detent housing 65. This engagement of the deck and detent teeth fixes the articulation position of the surgical fastening assembly 27 of the stapler. The slot depression 73 within the underside of the cap 70 of the actuator 37 frictionally receives the first and second detents, 43 and 44, of the deck 40.

Figure 13:
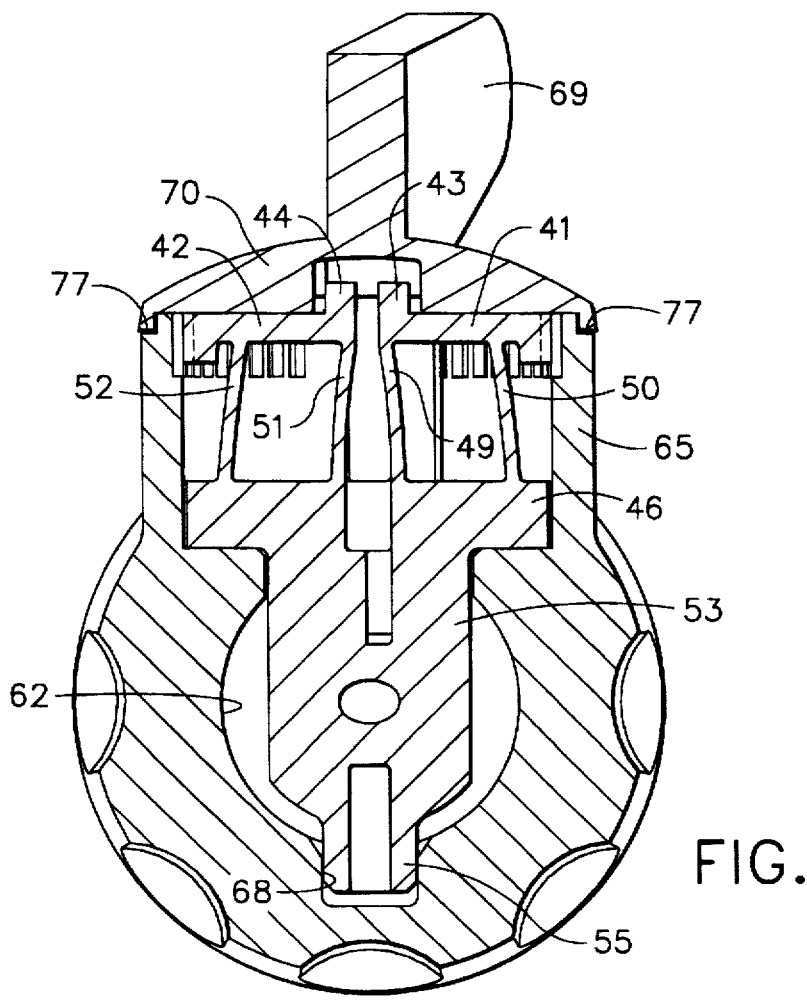
FIG. 13 is a transverse section of the articulation transmission assembly of FIG. 12 in which the articulation body of the assembly has been rotated from the locked position to an unlocked position for articulation of the surgical fastening assembly of the stapler.
Figure 14:
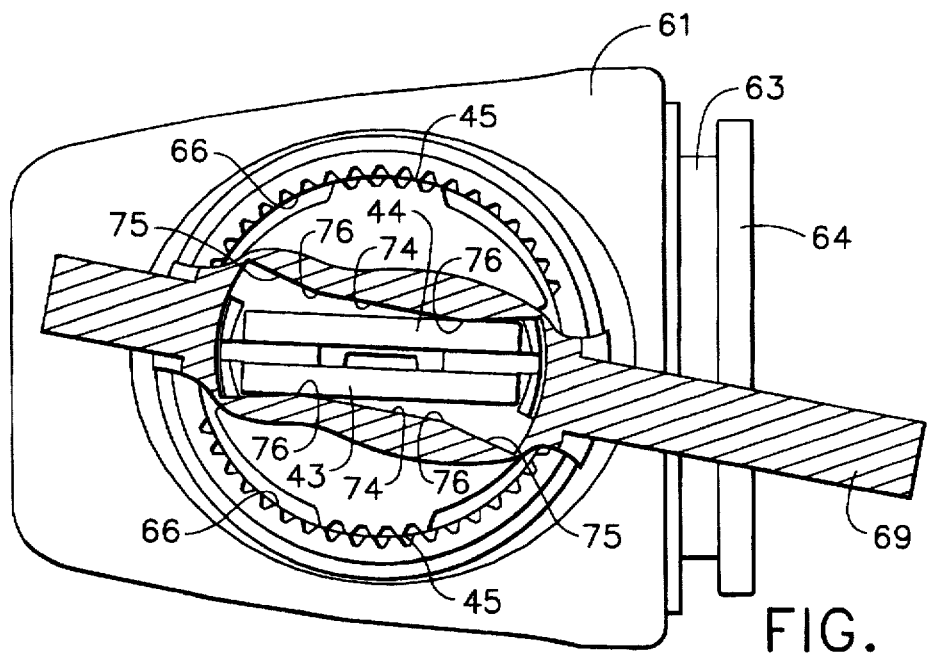
FIG. 14 is a plan view similar to FIG. 11 except that the articulation body has been rotated to the unlocked position.
Figure 15:
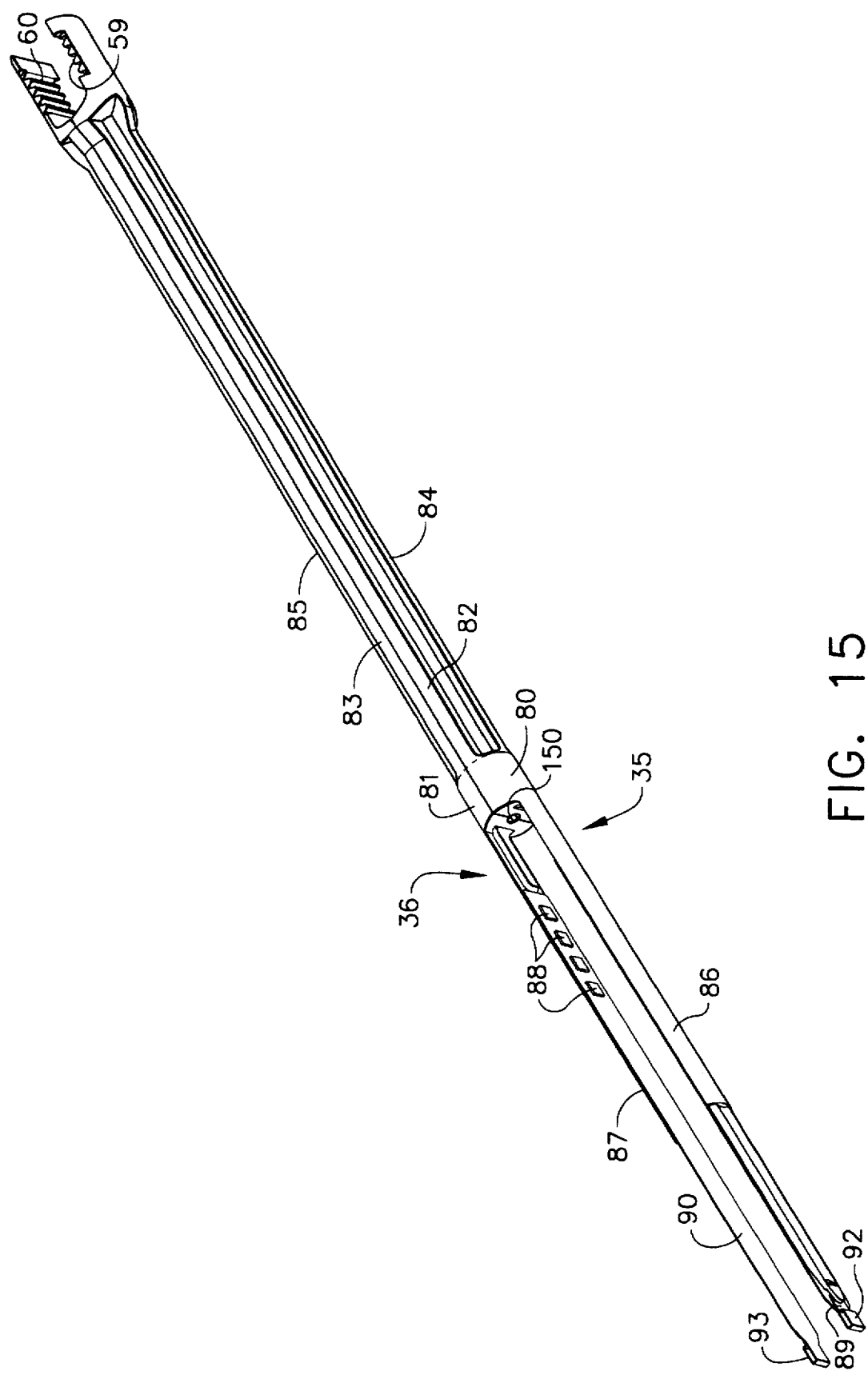
FIG. 15 is a perspective view of the preferred transmission band assemblies of the flexible neck assembly for articulating the surgical fastening assembly of the stapler.
Figure 20:
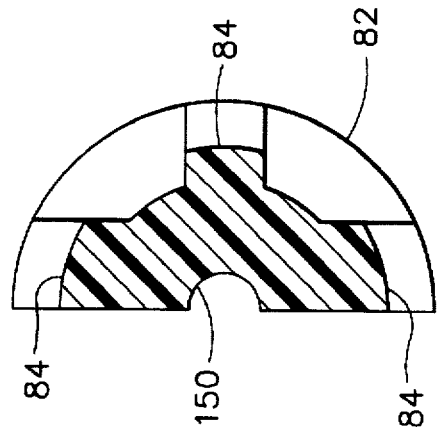
FIG. 20 is a section view taken along line 20—20 of FIG. 19.
Figure 21:
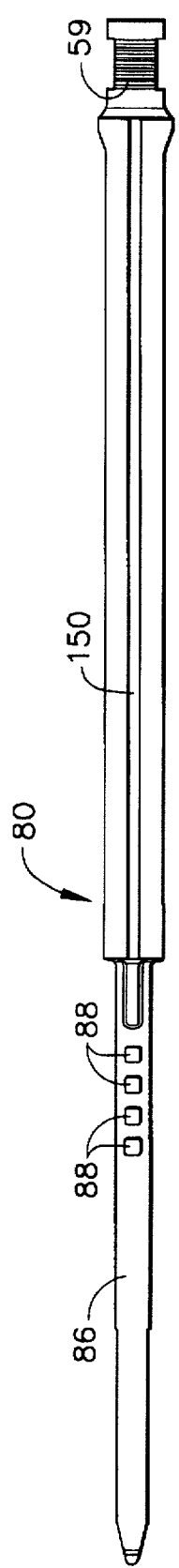
FIG. 21 is an interior side elevation view of the first transmission band of FIG. 18.
Figure 23:
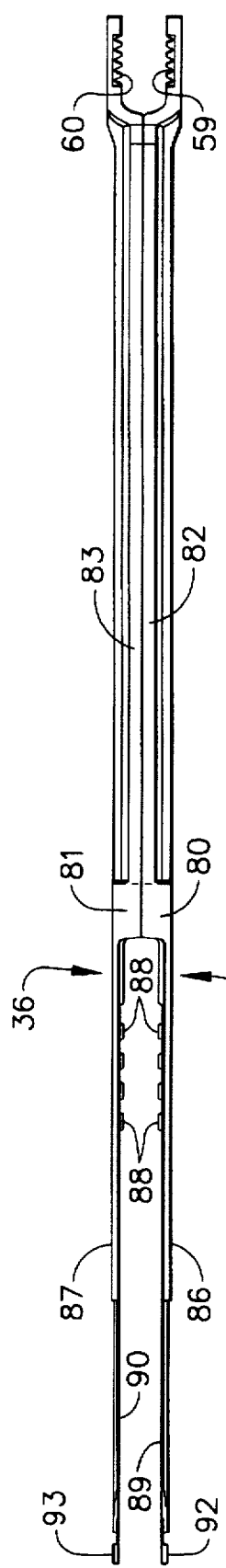
FIG. 23 is a plan view of the transmission band assemblies of FIG. 15.

Referring now to FIGS. 13 and 14, there is shown the articulation transmission assembly in an unlocked position. In the unlocked position, the deck teeth are decoupled and disengaged from the detent teeth. The unlocked positions of the articulation transmission assembly are spaced between the locked positions of the assembly. When a rotational force is applied to the lever arm 69 of the cap 70, the pressure points 76 at the junction between the diagonal flats 75 and the parallel slot walls 74 urge the first and second detents, 43 and 44, of the deck toward each other. As the detents are urged toward each other, the first and second deck halves, 41 and 42, of the deck are effectively compressed toward each other to enable the withdrawal of the deck teeth from engagement with the detent teeth within the detent housing of the nozzle. When the deck and detent teeth are withdrawn and decoupled from each other, each tooth on the sets of deck teeth will snap into engagement with a respective tooth on the array of detent teeth unless additional rotational force is applied to the lever arm of the actuator. If additional force is applied, the pressure points within the slot depression of the cap will continue to urge the deck halves toward each other, and ratcheting rotation will occur and continue until the rotational force is released.

Accordingly, ratcheting rotation of the articulation transmission assembly is provided, correspondingly causing articulation of the surgical fastening assembly in a plurality of discrete positions angled from the longitudinal axis of the endoscopic shaft of the stapler. The compression of the deck in response to rotational movement of the lever reduces the force the user must apply to articulate the surgical fastening assembly relative to the force which must be overcome to cause an articulation of the surgical fastening assembly when pressure is applied directly to the surgical fastening assembly.

Furthermore, when the articulation body 38 is rotated in a first direction in response to rotational movement of the actuator 37 to cause articulation of the surgical fastening assembly in that first direction, a rotational position will be reached where the rotational stops 47 of the base 46 of the articulation body abut the pair of ledges 78 protruding from the floor 67 of the detent housing 65. Consequently, further rotational movement of the articulation body in the first direction, and further articulation of the surgical fastening assembly in that first direction, is prevented. Consequently, the interaction of the rotation stops with the pair of ledges on the floor of the detent housing acts to limit the degree of rotational movement of the articulation body, and thus the degree of articulation of the surgical fastening assembly of the stapler.

Referring now to FIGS. 15-21 and 23, the details of the preferred transmission band assemblies are illustrated. The first and second transmission band assemblies, 35 and 36, have first and second transmission bands, 80 and 81, respectively. Each transmission band has an elongated structural portion, 82 and 83. When the bands are brought into contact with each other during assembly of the instrument, they form an elongated cylinder which has a longitudinal cavity 150 through it concentrically positioned between the bands for the passage of the firing rod, 57 (see FIG. 12). The first and second structural portions of the transmission bands have stiffening ribs, 84 and 85, to enhance structural support. At the proximal ends of the first and second bands, there are displayed the first and second racks, 59 and 60, which mate with the gear of the articulation transmission assembly. As discussed above, rotation of the gear converts the rotational movement of the articulation transmission assembly into longitudinal movement of the transmission band assemblies for articulation of the end effector.

The first and second transmission bands have exterior reinforcement band portions, 86 and 87, respectively, extending distally from the structural portions of the bands. Each exterior reinforcement band portion has a plurality of attachment lugs 88 for securing first and second interior articulation bands, 89 and 90. The transmission bands are preferably composed of a plastic, especially a glass fiber-reinforced amorphous polyamide, sold commercially under the trade name Grivory GV-6H by EMS-American Grilon. In contrast, it is desired that the interior articulation bands of the transmission band assembly be composed of a metal, advantageously full hard 301 stainless steel or its equivalent. The attachment lugs on the exterior reinforcement band portions of the transmission bands are received into and secured within a plurality of lug holes 91 on the corresponding interior articulation band.

At the distal end of the first and second interior articulation bands, there are first and second connector loops, 92 and 93, to couple the bands to the cartridge channel 29 (see FIGS. 24-26).

The remaining details of the preferred flexible neck assembly of the stapling instrument of this invention are shown in FIGS. 22 and 24-27. The flexible neck assembly is preferably composed of a rigid thermoplastic polyurethane sold commercially as ISOPLAST grade 2510 by the Dow Chemical Company. The flexible neck assembly 32 has the first and second flexible neck portions, 33 and 34. These neck portions are separated by a central longitudinal rib 94. The neck portions each have a plurality of neck ribs 95 configured essentially as semi-circular disks. Each neck rib has an interior plate 96 which is substantially perpendicular to the central longitudinal rib and parallel to an adjacent interior plate. Each neck rib also has a concave exterior dish 97 extending from its interior plate. As such, the flexible neck portions together generally form a cylindrical configuration. Separating the neck ribs are a plurality of kerfs 98. A side slot 99 extends through each of the neck ribs to provide a passage through the first and second flexible neck portions for receiving the interior articulation bands and exterior reinforcement band portions of the flexible bands. In a similar fashion, the central longitudinal rib separating the first and second flexible neck portions has a central longitudinal slot 100 for providing a passage to receive the stapler actuating members and if desired, a knife blade for cutting the tissue between the staple lines during or after firing.

Extending proximally from the first and second flexible neck portions, there are first and second support guide surfaces, 101 and 102, for supporting the reciprocating movement of the interior articulation bands and the exterior reinforcement portions of the flexible transmission band assemblies. Extending from the distal end of the flexible neck portions, there is a channel guide 103 for properly guiding the movement of the stapler actuating members into the staple cartridge of the stapling instrument.

As shown nicely in FIG. 22, when the flexible neck assembly is fully articulated, adjacent concave dishes 97 come into contact with each other. The spacing between adjacent dishes, and the size of each dish chosen, can provide a practical means for controlling the degree of articulation and the total amount of articulation achieved. In addition, the optimization of the design variables of the flexible neck assembly enables one of the transmission band assemblies to take a substantial load under compression during articulation while the other band assembly is concurrently taking a load under tension.

The proximal end of the cartridge channel (illustrated in FIG. 24) has a pair of band connector ears, 104 and 105. These band connector ears are inserted into and through the connector loops, 92 and 93, respectively, on the distal end of the interior articulation bands. In this manner, the cartridge channel which houses the staple cartridge is coupled to the interior articulation bands of the flexible neck assembly. FIG. 28a and 28b illustrates how the flexible neck assembly provides for the articulation of the end effector of the stapling instrument. Specifically, the reciprocation of the first and second flexible transmission band assemblies in opposite directions causes the interior articulation bands received into and through the side slots of the neck ribs on the flexible neck portions to reciprocate in a like manner. Upon reciprocation of the interior articulation bands, in particular when the first band is moved proximally in tandem with the second band moving distally as illustrated in FIG. 28, the first and second flexible neck portions bend as the neck ribs of the first flexible neck portion move toward each other and the neck ribs of the second flexible neck rib portion concurrently move away from each other. The coupling of the interior articulation band to the exterior reinforcement band portion of the transmission band prevents the interior articulation band from buckling between adjacent neck ribs.

Although this invention has been described in connection with its most preferred embodiment, numerous additional embodiments will become readily apparent to those skilled in the art. For example, although the invention has been described in connection with an articulating endoscopic stapler, the invention is equally applicable to conventional open surgical instruments. Additionally, although the invention has been described in connection with an articulation transmission assembly and flexible neck assembly which provides for remote articulation of a surgical fastening assembly, it is equally applicable to an instrument which provides remote articulation of a different kind of end effector. Accordingly, the preferred embodiment described in connection with this detailed description is intended to illustrate the invention only, and is not in any way intended to limit the scope or spirit of the claimed invention.

What is claimed is:

1. An articulating surgical instrument comprising:
 a) a frame including a hand grip for gripping and manipulating said instrument at a first end of said instrument;

b) a shaft extending from said frame, said shaft having a longitudinal axis;

c) an end effector at an opposite end of said instrument for manipulating tissue to carry out a desired surgical function, said end effector being movable to provide articulation of said end effector from a first position generally parallel to said shaft longitudinal axis to a second position angled from said shaft longitudinal axis; and d) a flexible neck assembly coupled to a proximal end of said end effector for articulating said end effector from said first position to said second position, said flexible neck assembly including:

i) first and second flexible neck portions separated by a central longitudinal rib therebetween, each of said flexible neck portions having a plurality of neck ribs extending from said longitudinal rib and a plurality of kerfs separating each of said neck ribs from an adjacent neck rib, and each of said neck ribs having a side slot therethrough; and ii) first and second transmission band assemblies received within each said side slot of said neck ribs of said first and second flexible neck portions for reciprocating movement therein, each of said transmission band assemblies having an interior articulation band and an exterior reinforcement band attached thereto;

wherein when said first and second transmission band assemblies are reciprocated in opposite directions within each said side slot of said neck ribs of said first and second flexible neck portions of said flexible neck assembly, said end effector is articulated from said first position to said second position.

2. The instrument of claim 1 further comprising an articulation transmission assembly spaced from said flexible neck assembly and coupled to said first and second transmission band assemblies for effecting reciprocating movement of said transmission band assemblies.

3. The instrument of claim 2 wherein each of said neck ribs is configured as a semi-circular disk.

4. The instrument of claim 3 wherein each said disk includes an interior plate extending generally perpendicularly from said central longitudinal rib and parallel to an adjacent interior plate, and a concave exterior dish extending from said interior plate.

5. The instrument of claim 4 wherein said flexible neck assembly has first and second spaced-apart supporting guide surfaces extending proximally from said first and second flexible neck portions, and said first and second flexible band assemblies slide on said first and second support guide surfaces for supporting thereon.

6. The instrument of claim 5 wherein said central longitudinal rib has a central slot therethrough.

7. The instrument of claim 6 wherein said shaft is an elongated shaft, and said instrument is adapted for endoscopic surgery.

8. The instrument of claim 7 wherein said end effector is a surgical fastening assembly.

9. An articulating surgical instrument comprising:

a) a frame including a hand grip for gripping and manipulating said instrument at a first end of said instrument;

b) a shaft extending from said frame, said shaft having a longitudinal axis;

c) an end effector at an opposite end of said instrument for manipulating tissue to carry out a desired surgical function, said end effector being movable to provide articulation of said end effector from a first position generally parallel to said shaft longitudinal axis to a second position angled from said shaft longitudinal axis;

d) a flexible neck assembly coupled to a proximal end of said end effector for articulating said end effector from said first position to said second position, said flexible neck assembly including:

i) first and second flexible neck portions separated by a central longitudinal rib therebetween, each of said flexible neck portions having a plurality of neck ribs configured as semi-circular disks extending from said central longitudinal rib and a plurality of kerfs separating each of said neck ribs from an adjacent neck rib, each of said neck ribs having a side slot therethrough, and each of said semi-circular disks of said neck ribs having an interior plate extending generally perpendicularly from said central longitudinal rib and parallel to an adjacent interior plate, and a concave exterior dish extending from said interior plate; and ii) first and second transmission bands received within each said side slots of said neck ribs of said first and second flexible neck portions for reciprocating movement therein;

wherein when said first and second transmission bands are reciprocated in opposite directions within each said side slot of said neck ribs of said first and second flexible neck portions of said flexible neck assembly, said end effector is articulated from said first position to said second position.

10. The instrument of claim 9 further comprising an articulation transmission assembly spaced from said flexible neck assembly and coupled to said first and second transmission bands for effecting reciprocating movement of said transmission bands.

11. The instrument of claim 10 wherein said central longitudinal rib has a central slot therethrough.

12. The instrument of claim 11 wherein said shaft is an elongated shaft, and said instrument is adapted for endoscopic surgery.

13. The instrument of claim 12 wherein said end effector is a surgical fastening assembly.

* * * * *